United States Patent [19]

Kung

[11] Patent Number: 5,079,346
[45] Date of Patent: Jan. 7, 1992

[54] GALLIUM-LABELLED IMAGING AGENTS

[75] Inventor: Hank F. Kung, Wynnewood, Pa.

[73] Assignee: Trustees of the University of Pennsylvania, Philadelphia, Pa.

[21] Appl. No.: 517,219

[22] Filed: May 1, 1990

[51] Int. Cl.$^5$ .................. C07F 5/00; A61K 49/02
[52] U.S. Cl. .................................. 534/10; 424/1.1
[58] Field of Search ........................ 424/1.1; 534/10

[56] References Cited

U.S. PATENT DOCUMENTS 4,885,363 12/1989 Tweedle et al. ................. 534/10 X

OTHER PUBLICATIONS

Green, Mark A. and Welch, Michael J. "Review—Gallium Radiopharmaceutical Chemistry", Nucl. Med. Biol., vol. 16, No. 5, pp. 435–448 (1989).

Kung, H. F., et al., "Synthesis of New Bis(aminoethanethiol) (BAT) Derivatives: Possible Ligands for $^{99m}$Tc Brain Imaging Agents", J. Med. Chem., 1985, 28, 1280.

Liu, B. L., Kung, H. F., Jin, Y. T., Zhu, L., and Meng, M.: A new myocardial imaging agent: synthesis, characterization and biodistribution of [$^{113m}$In]TE-BAT. J. Nucl. Med. 30:367–373, 1989.

Green, M. A., Welch, M. J., Mathias, C. J., et al.: Gallium-68 1,1,1-tris (5-methoxysalicylaldiminomethyl) ethane: A potential tracer for evaluation of myocardial blood flow, J. Nucl. Med. 26:170–180, 1985.

Green, M. A., Klippenstein, D. L., Tennison, J. R.: Copper (II) bis(triosemicarbazone) complexes as potential tracers for evaluation of cerebral and myocardial blood flow with PET, J. Nucl. Med. 29: 1549–1557, 1989.

Primary Examiner—John S. Maples
Attorney, Agent, or Firm—Woodcock, Washburn, Kurtz, Mackiewicz & Norris

[57] ABSTRACT

Complexes having the formula:

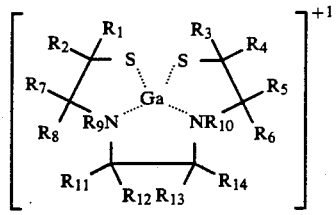

where each of $R_1$–$R_{14}$ is independently selected from the group consisting of hydrogen, alkyl groups in which one or more carbon atoms is optionally substituted by a heteroatom such as N, O or S, and phenyl optionally mono- or di-substituted with a substituent selected from the group consisting of —$SR_{15}$,— $OR_{15}$, and —$NR_{15}R_{16}$, where $R_{15}$ and $R_{16}$ are independently selected from H and alkyl groups; or each grouping of $R_1$ and $R_2$, $R_3$ and $R_4$, $R_5$ and $R_6$, $R_7$ and $R_8$, $R_{11}$ and $R_{12}$, and $R_{13}$ and $R_{14}$ may independently be taken together to form a cyclic alkyl in which one or more carbon atoms is optionally substituted by a heteroatom, and Ga is a radioactive gallium isotope, and pharmaceutically acceptable salts thereof prepared from gallium radioiosotopes and ligands such as tetraethylcyclohexyl-bisaminoethanethiol (BAT-TECH) are disclosed which, because of their high uptake in the heart and lipid-solubility, should be useful for myocardial perfusion imaging.

17 Claims, No Drawings

GALLIUM-LABELLED IMAGING AGENTS

BACKGROUND OF THE INVENTION

This invention relates to novel imaging agents for positron emission tomography (PET) and, more specifically, to novel lipid-soluble gallium complexes which should possess utility as myocardial imaging agents.

Positron emission tomography (PET) is a technique whereby a three-dimensional reconstruction of in vivo radionuclide distribution is possible, providing images that map and quantitate tissue activity levels. The demand for new and novel positron-emitting radiopharmaceuticals continues to increase as more institutions acquire instrumentation for PET imaging.

There are two gallium radioisotopes, Ga-67 and Ga-68. Both of these gallium radioisotopes possess nuclear properties that make them attractive for use in nuclear medicine. The first, Ga-67, is cyclotron-produced and is commercially available as gallium chloride and gallium citrate. The second, Ga-68, has the distinction of being one of the few short-lived positron emitting radionuclides available from a parent/daughter generator system. The Ge-68/Ga-68 generator is commercially available and is attractive because of its relatively long parent half-life (287 days) and convenient daughter half-life (68 min.). The generator-based radiopharmaceuticals may provide a useful and effective way of PET imaging without an on-site cyclotron.

Numerous gallium-68 radiopharmaceuticals have been reported, and some are in routine use for human studies. Unfortunately, development of lipophilic gallium-68 tracers for perfusion imaging of the brain and heart has not been successful. There are tris(salicylaldimine) complexes of gallium that might be used for evaluation of myocardial perfusion. (Green, M. A. and Welch, M. J.: Synthesis and crystallographic haractyerization of a gallium salicylaldimine complex of radiopharmaceutical interest. J. Am. Chem. Soc. 106:3689, 1984; Green, M. A., Welch, M. J., Mathias, C. J., et al: Gallium-68 1,1,1-tris (5-methoxysalicylaldiminomethyl)ethane: A potential tracer for evaluation of myocardial blood flow. J. Nucl. Med. 26:170-180, 1985; Green, M. A.: Synthesis and biodistribution of a series of lipophilic gallium-67 tris(salicylaldimine) complexes. J. Labeled Compounds Radiopharm 23:1221-1222, 1986). However, these agents proved to be unsuitable for clinical use as myocardial perfusion imaging agents because they behave neither as freely diffusible tracers nor as microsphere analogs. Neutral and highly lipid soluble Ga-LICAM complexes have been reported. (Moerlein, S. M., Welch, M. J., Raymond, K. N.: Use of tricate cholamine legends to alter the biodistribution of gallium-67. J Nucl. Med. 23:501-506, 1982). These complexes showed little brain uptake, which suggests that lipid-solubility is not the sole requirement for molecules to penetrate the intact blood-brain barrier. No gallium tracers have been developed that effectively cross the barrier for cerebral blood flow studies.

Despite its short half-life, 75 seconds, the Rb-82, produced by a Sr-82/Rb-82 generator, is quite useful for assessment of myocardial perfusion. (Goldstein, R. A., Mullani, N. A., Wong, W. H., et al: Positron imaging of myocardial infarction with rubidium-82. J. Nucl. Med. 27:1824-1829, 1986; Gould, K. L., Goldstein, R. A., Mullani, N. A.: Economic analysis of clinical positron emission tomography of the heart with rubidium-82. J. Nucl. Med., 30:707-717, 1989). The generator produced agent can support clinical cardiac PET imaging without an on-site cyclotron. A comparable Ga-68 compound with a half-life of 68 minutes may provide significant improvements for PET myocardial imaging.

The zinc-62/copper-62 radionuclide generator (Robinson G. D.: Generator systems for positron emitters. In Positron Emission Tomography, Reivich, M., Alavi, A., eds., A R Liss, New York, 1985, pp 81-102; Robinson, G. D., Zielinski, F. W., Lee A. W.: Zn-62/Cu-62 generator: a convenient source of copper-62 radiopharmaceuticals. Int. J. Appl. Radiat. Isotopes 31:111-116, 1980; Thakur, M. L., Nunn, A. D.: Preparation of carrier-free zinc-62 for medical use. Radiochem. Radioanal. Letters 2:301-306, 1969; Ueda, N., Nakamoto, S., Tanaka, Y., et al.: Production of Zn-62 and development of Zn-62/Cu-62 generator system. J. Nucl. Med. 24:P124, 1983) is also a possible source of radiopharmaceuticals for diagnostic imaging by PET in locations that lack an in-hospital cyclotron for radionuclide production. The potential of this generator to provide clinically useful copper-62 radiopharmaceuticals has been reported. (Robinson, G. D., Zielinski, F. W., Lee, A. W.: Zn-62/Cu-62 generator: a convenient source of copper-62 radiopharmaceuticals. Int. J. Appl. Radiat. Isotopes 31:111-116, 1980; Thakur, M.L., Nunn, A.D.: Preparation of carrier-free zinc-62 for medical use. Radiochem. Radioanal. Letters 2:301-306, 1969; Ueda, N., Nakamoto, S., Tanaka, Y., et al.: Production of Zn-62 and development of Zn-62/Cu-62 generator system. J. Nucl. Med. 24:p124, 1983). The principal disadvantages of the Zn-62/Cu-62 generator system are the rather short (9 hour) half-life of the cyclotron-produced parent, which means that the generator is useful for only one to two days. Nonetheless, the clinical potential of a series of copper(II) bisthisemicarbazone complexes, specifically Cu(PTSM), as myocardial and perfusion tracers have been demonstrated. (Green, M. A., Klippenstein, D. L., Tennison, J. R.: Copper (II) bis(thiosemicarbazone) complexes as potential tracers for evaluation of cerebral and myocardial blood flow with PET. J. Nucl. Med. 29:1549-1557, 1989; Green, M. A.: A potential copper radiopharmaceutical for imaging the heart and brain: copper-labeled pyruvaldehyde bis(N4-methylthiosemicarbazone). Nucl. Med. Biol., Int. J. Radiat. Appl. Instrum. Part B 14:59-61, 1989). The Cu(PTSM) is based on an $N_2S_2$ ligand and is a neutral and lipid-soluble compound. After an intravenous injection, the compound passes through the cell membrane, including the intact blood-brain barrier. Apparently, the compound decomposes intracellularly after interacting with sulfurhydryl groups. (Baerga, I. D., Maickel, R. P. and Green, M. A.: Subcellular distribution of tissue radiocopper following intravenous administration of [Cu-62]-Cu(PTSM). J. Nucl. Med. 30:920, 1989 (Abstract No. 812). The regional distribution is a reflection of regional perfusion, a property consistent with "chemical microspheres". Therefore, this agent in combination with the Zn-62/Cu-62 generator may provide a convenient source of radiopharmaceuticals for measuring regional blood perfusion of the brain and heart. However, Ga-68 labeled compounds may offer some advantages because the longer half-lives of the parent and daughter may greatly enhance the clinical potential as PET radiopharmaceuticals.

Recent advances in Tc-99 chemistry of complexes based on $N_2S_2$ ligands have dramatically enhanced our ability to predict the chemical structure of the final Tc-99m complexes. This series of ligands form strong complexes with (Tc=O)$^{+3}$. The x-ray crystallography studies of several N$_2$S$_2$ complexes have confirmed the (Tc=O)$^{+3}$ chemical state and the pyramidal core structure.

The use of N$_2$S$_2$ ligands to investigate the radiochemistry of indium, a plus three cation, has also been investigated. In particular, a unique indium complex, [$^{113m}$In]TE-BAT (tetraethyl-bis-aminoethanethiol) was evaluated, indicating that the complex, when labeled with $^{111}$In, may show promise as a possible tracer for myocardial perfusion imaging. (Liu, B-L, Kung, H. F., Jin, Y. T., Zhu, L., and Meng, M.: A new myocardial imaging agent: synthesis, characterization and biodistribution of [$^{113m}$In]TE-BAT. J. Nucl. Med. 30:367-373, 1989).

SUMMARY OF THE INVENTION

It has now been found that stable complexes can be prepared from gallium radioisotopes and the ligand tetraethyl-cyclohexyl-bis-aminoethanethiol (BAT-TECH) or analogs thereof. That such stable complexes could be prepared was highly surprising in view of the fact that gallium ions usually prefer "hard" donor atoms, such as oxygen, rather than nitrogen, and that stable complexes of gallium generally require more than four covalent bonds to the ion. See, for example, Green MA et al., Nucl. Med. Biol., Vol. 16, No. 5, pp. 435-448 (1989).

This invention therefore relates to complexes of the formula:

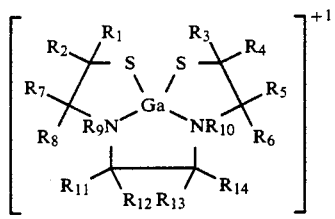

where each of R$_1$-R$_{14}$ is independently selected from the group consisting of hydrogen, alkyl groups in which one or more carbon atoms is optionally substituted by a heteroatom such as N, O or S, and phenyl optionally mono- or di-substituted with a substituent selected from the group consisting of —SR$_{15}$, —OR$_{15}$, and —NR$_{15}$R$_{16}$, where R$_{15}$ and R$_{16}$ are independently selected from H and alkyl groups; or each grouping of R$_1$ and R$_2$, R$_3$ and R$_4$, R$_5$ and R$_6$, R$_7$ and R$_8$, R$_{11}$ and R$_{12}$, and R$_{14}$ and R$_{14}$ may independently be taken together to form a cyclic alkyl in which one or more carbon atoms is optionally substituted by a heteroatom. Also included within the scope of this invention are pharmaceutically acceptable salts of the complexes of Formula I, such as chloride or bromide salts.

Tests indicate that complexes of Formula I are lipid-soluble, and that the compounds exhibit high uptake in the heart as well as in the liver. The complexes should therefore be useful as tracers for myocardial perfusion imaging. Since they may be prepared using Ga-68 isotopes, the complexes of the invention also offer the advantage of being available to institutions not having the use of an on-site cyclotron.

DETAILED DESCRIPTION OF THE INVENTION

The ligands which are used in preparing the gallium complexes of this invention may be prepared by methods known in the art, e.g., by the method disclosed, or by methods analogous to that disclosed, by Kung HF, Molnar M, Billings J, Wicks R, Blau M., "Synthesis and Biodistribution of Neutral Lipid-Soluble Tc-99m Complexes Which Cross the Blood Brain Barrier", J. Nucl. Med. 25:326-332 (1984), the disclosure of which is hereby incorporated by reference.

Each of R$_1$-R$_{14}$ may be selected from H, from alkyl groups, preferably having up to ten carbon atoms, or pairs of R$_1$ and R$_2$, etc., may be taken together to form a cycloalkyl group, such as cyclohexyl. Each of R$_1$-R$_{14}$ may also be a phenyl group, optionally substituted with one or two groups selected from the group consisting of —SR$_{15}$, —OR$_{15}$, and —NR$_{15}$R$_{16}$, where R$_{15}$ and R$_{16}$ are independently selected from H and alkyl groups, generally alkyl groups having up to ten carbon atoms.

For reasons of ease of synthesis, it is preferred that, in the ligands from which the complexes of Formula I are prepared, R$_1$=R$_2$; R$_3$=R$_4$; R$_5$=R$_6$; R$_7$=R$_8$; R$_{11}$=R$_{12}$ and R$_{12}$ and R$_{13}$=R$_{14}$ or each grouping of R$^1$ and R$_2$, R$_3$ and R$_4$, R$_5$ and R$_6$, R$_7$ and R$_8$, R$_{11}$ and R$_{12}$, and R$_{13}$ and R$_{14}$ be taken together to form a ring structure. More preferred complexes of Formula I are those in which, independently, (1) R$_5$, R$_6$, R$_7$, R$_8$, R$_{13}$ and R$_{14}$ are each hydrogen; (2) R$_1$, R$_2$, R$_3$ and R$_4$ each is an ethyl group; and (3) R$_{11}$ and R$_{12}$ are taken together to form a cyclohexyl group. The preferred complex according to this invention is the [Ga(BAT-TECH]=complex.

Gallium (Ga=$^3$) reacts with the bisaminoethanethiol (BAT) ligands and their analogs in millimolar quantities under aqueous conditions. The labelling reaction is pH sensitive, the optimum pH range being within 2.5-5, preferably between 3 and 4. At higher pH, precipitation of the ligand, due to the limited solubility in water, is observed. This pH can be easily maintained by the addition of buffer solution and is therefore easily adaptable for a simple, one step reaction. both the reaction temperature and the concentration of the ligand in the reaction mixture affect the labeling yield. Best yields are obtained utilizing a reaction temperature above about 40° C. and a ligand concentration above about 3 mg/ML.

Tests indicate that the complex formation between Ga$^{+3}$ and BAT-TECH ligand is very rapid, simple and occurs in high yield ($\geq$ 95%). The gallium ion and the BAT-TECH appear to form a 1:1 complex with release of two hydrogen ions and the net charge of the no-carrier-added [$^{67}$Ga]BAT-TECH is probably +1. The high labeling efficiency and excellent purity of this labeling reaction requires no further purification before animal study.

The [$^{67}$Ga]BAT-TECH displays fast myocardial uptake and rapid blood and lung washout in rats. The biological behavior of the complex suggests that this agent, as well as related complexes within the scope of Formula I herein and those labeled alternatively with $^{68}$Ga, should be useful for myocardial perfusion imaging.

Due to the high yield and rapid formation of the complexes of this invention, they should lend themselves easily to formation from materials which could be provided to users in kits. Kits for forming imaging agents would contain, for example, a vial containing a physiologically suitable solution of the appropriate ligand in a concentration and at a pH suitable for optimal complexing conditions. The user would add to the vial an appropriate quantity of gallium radioisotope, preferably $^{68}Ga$, and subject the resulting reaction mixture to temperatures to promote the complexing reaction. The resulting solution of gallium complex could be used directly in the patient for PET imaging.

EXAMPLE 1

PREPARATION OF 2,9-DIMETHYL-2,9-DIMERCAPTO-5-(2-HYDROXYPHENYL)-4,7-DIAZADECANE

This preparation was achieved by a method reported previously. Kung HF, Molnar M, Billings J, Wicks R, Blau M., "Synthesis and Biodistribution of Neutral Lipid-Soluble 99m Complexes Which Cross the Blood Brain Barrier", J. Nucl. Med. 25:326-332 (1984).

A. Preparation of α-Amino-2-methoxybenzen-acetonitrile

To a solution of 50.0 g (1.0 mol) of sodium cyanide, 53.5 g (1.0 mol) of ammonium chloride, and 60 mL of concentrated ammonium hydroxide in 400 mL of water was added 125 g (0.92 mol) of o-anisaldehyde in 400 aromatic C-C); of dry methanol. After the mixture was stirred for 3 h at 23° C., the methanol was removed under reduced pressure, and the residual solution containing the crude product was diluted with 500 mL of water and extracted with methylene chloride (2×400 mL), dried over sodium sulfate, and filtered; the solvent was subsequently removed under vacuum to give an orange oil. By means of column chromatography on silica gel using ethyl acetate as the eluent, the o-amino nitrile compound (A) was separated from the starting material and the side products; IR (neat) 2240 (w, —C≡N), 1600, 1500 cm$^1$(s, aromatic C=C); NMR (CDCL$_3$) 1.03 (2 H, s, NH$_2$), 3.90 (3 H, s, OCH$_3$), 5.05 (1 H, s, CH), 7.15 (4 H m, ArH). The α-amino nitrile (yellow oil) was unstable as a free base; therefore it was either used immediately for the next reaction or converted to the tartarate salt.

B. Preparation of D-α-amino-2-methyoxybenzeneacetonitrile d-Hemitartarate

To a solution of crude compound (A) prepared freshly from 62.5 g (0.46 mol) of o-anisaldehyde in 1 L of benzene-methanol (4:1) was added 60 g (0.40 mol) of d-tartaric acid dissolved in 400 mL of methanol. The resultant flocculent precipitate was filtered, washed with benzene-methanol (2:1), suspended in carbon tetrachloride, filtered, and dried to produce 80 g (0.26 mol, 55.7%) of dense white powder, (B), mp 218° C. A small sample was recrystallized twice from methanol for elemental analysis: mp 218 degrees C (dec.). Anal. ($C_{13}N_{16}N_2O_7$·$\frac{1}{2}CH_3OH$) C, H, N.

C. Preparation of α-(Acetylamino)-2-methoxybenzeneacetonitrile

Compound (B) (28.0 g, 89.7 mmol) was dissolved into 250 mL of aqueous sodium bicarbonate, pH 8.0, was extracted with methylene chloride (2×150 mL). The combined methylene chloride solution was dried over sodium sulfate (anhydrous), filtered, and reduced to approximately 50 mL of light yellow solution under vacuum. This solution was slowly added to 14.6 g (142 mol) of acetic anhydride at 0° C. and then stirred for 2 hours at room temperature, after which excess volatiles ($CH_2Cl_2$, HOAc, $Ac_2O$) were removed under vacuum. The residue was recrystallized 2 times from ethyl acetate-hexane (1:1) to give 10.65 g (48.1 mmol) of white microcrystalline powder (C); mp 139-140°; IR 3450 (m, N-H), 1695 (s, amide), 1600, 1500 (aromatic C=C), 2250 cm$^{-1}$ (w, C≡N); NMR (CDCl$_3$) 2.00 (3 H, s, O-CCH$_3$), 3.93 (3 H, s, OCH$_3$), 6.13 (1 H, d, J$_1$=9 Hz, Ch), 7.10 (5 H, m, ArH+NH), Anal. ($C_{11}H_{12}N_2O_2$) C, H, N, O.

D. Preparation of α-Amino-2-methyoxybenzene-ethanamine

To a cold (0° C.) solution of 34.0 g (0.90 mol) of LiAlH$_4$ in 300 mL of dry THF under N$_2$ was added dropwise crude dry compound (C) dissolved in 200 mL of dry THF, freshly prepared from 125 g (0.92 mol) of α-anisaldehyde. After the mixture was stirred 12 h at room temperature, the excess hydride was decomposed with 1 L of wet THF-ether. The alumina was filtered off, and the organic solvents were evaporated under vacuum to produce approximately 200 mL of an orange oil. The crude product was azeotropically dried with benzene and then fractionally distilled under vacuum (0.5-0.25 torr). The clear oil (distilled at 96-125° C.), which represented the majority of the distillate, was found to be primarily 2-(aminomethyl)anisole. The minor fraction (distilled at 124°-140° C.), (D), approximately 15 mL, was used without further purification. IR (disappearance) 2250 cm$^{-1}$, NMR (DCDl$_3$) 1.57 (4 H s, NH$_2$), 2.93 (2 H, m, NCH$_2$), 3.77 (3 H, s, ArOCH$_3$), 4.12 (1 H, t, J$_1$=6 Hz, NCH), 7.05 (4 H, m, ArH). Anal. ($C_9H_{14}N_2O$) C, H, N, O.

E. Preparation of α-(Acetylamino)-2-methoxybenzeneethanacetamide

To a cold (0° C.) solution of 1.0 g (9.8 mmol) of acetic anhydride in 50 mL of ethyl acetate was slowly added approximately 1 mL (5 mmol) of enriched distillate of compound (D). After the mixture was stirred for 2 h at room temperature, the volatile organics were removed under vacuum to leave a white solid. The residue was recrystallized from ethanol-ethyl acetate to yield 1.0 g (66%) of white crystals, (E); mp 199° C.; IR (KBr) 3310 (s, N-H), 1640 cm$^{-1}$ (2, C=), amide 1 band); NMR (CDCl$_3$) 1.97 (6 H d, J$_1$=3 Hz, NAc), 3.47 (2 H m, NCH$_2$), 3.85 (3 H, s, ArOCH$_3$), 5.27 (1 H, m, NCH), 6.20 (1 H, m, NH), 7.03 (5 H, M, ArH+NH). Anal. ($C_{13}H_{18}N_2$), C, H, N, O.

F. Preparation of 3,3,10,-Tetramethyl-1,2-dithia-7-(2-methoxyphenyl)-5,8-diazacyclodeca-4,8-diene To a solution of 6.01 g (29.6 mmol) of 2,2′-dithiobis(2-methylpropanal) in 25 mL of absolute ethanol was added 5.0 g (30.0 mmol) of distilled compound (E). The solution was stirred at 50° C. for 30 min and subsequently allowed to stand for 12 h at 4° C., after which a precipitate formed. The precipitate was washed with cold methanol and dried to yield 6.52 g (19.4 mmol, 65.5%) of white powder (F). An analytical sample was recrystallized once from ethyl acetate; mp 121° C.; IR (KBr) 1650 (s, C=N), 1600, 1495 cm$^{-1}$, (w, Ar); NMR (CDCl$_3$) 1.43 (12 H, d, J = 10 Hz, C(CH$_2$)$_2$), 2.90 (1 H, t, J$_1$=9 Hz, NCH), 3.83 (3 H, s, OCH$_3$), 4.58 (2 H, m, NCH$_2$), 7.00 (5 H, m, ArH+N=CH), 7.77 (1H, m, ArH). Anal. ($C_{17}H_{24}N_2OS_2$) C, H, N.

G. preparation of 2,9-Dimethyl-2,9-dimercapto-5-(2-methyoxyphenyl)-4,7-diazadecane Hydrochloride To a solution of 45 mL (153 mmol) of Red-Al (Aldrich Chemical Co.) in 200 mL of dry benzene under $N_2$ was added dropwise 7.0 g (20.8 mmol) of compound (F) dissolved in 10 mL of dry benzene. After refluxing for 1 h, the solution was chilled to 0° C. and excess hydride decomposed by the slow addition of 50 mL of concentrated HCl. The pH was adjusted to 10 with concentrated aqueous NaOH. The solids were removed via filtration and the benzene evaporated under vacuum to produce a foul-smelling purple oil. The oil was dissolved into 60 mL of absolute ethanol at 0° C., and compound was caused to precipitate by bubbling dry HCl gas. The precipitate was filtered, rinsed with ethanol, and dried to produce 5.95 g (68.8%) of white powder (G). An analytical sample was prepared by recrystallization once from ethanol: mp 182-188° C.; IR (neat) 3300 (w, NH st), 2550 cm$^{-1}$ (w, SH str); NMR (CDCl$_3$) (free base) 1.37 (12 H, s, C(CH$_3$)$_2$) 2.00 (4 H, s, SH, NII), 2.65 (6 H, m, NCH,), 3.82 (3 H, s, ArOCH$_3$), 4.13 (1 H, m, NCH), 7.13 (4 H, m, ArH). Anal. (C$_{17}$H$_{30}$N$_2$OS$_2$) C, H, N, S.

H. Preparation of 2,9-Dimethyl-2,9-merapto-5-(2-hydroxyphenyl)-4,7-diazadecane To a suspension of compound (G), 5.95 g (14.3 mmol) in 60 mL of absolute ethanol was added a solution of 0.6 g (26.8 mmol) of sodium in 20 mL of absolute ethanol. After the mixture was stirred for 30 minutes, the sodium chloride was filtered off and the solvent removed under vacuum to produce the free-base form of compound (G) as a clear oil in quantitative yield. The oil (4.89 g, 14.3 mmol) was dissolved into 50 mL of CH$_2$Cl$_2$ at 0° C. and added dropwise to boron tribromide (72 mmol in 72 mL of CH$_2$Cl$_2$) at 0° C. under $N_2$. After addition, the solution was revlused for 12 h, then allowed to cool to room temperature, and treated with 200 mL of water. The aqueous phase was adjusted to pH 8 with NaHCO$_3$, and the methylene chloride layer was separated, dried over Na$_2$SO$_4$, and filtered; the solvent was evaporated under vacuum to produce a crimson oil (5.3 g) that solidified upon standing for 12 hours at room temperature. The crude solid was washed with hexane 2-propanol (2×5 ml) and multiple recrystallizations yielded a foul-smelling white powder; yield 0.484 g (10.3%); mp 85° C.; IR (CCl$_4$) 3370 (2, NH str), 1600 cm$^{-1}$ (m, Ar str); NMR (CDCl$_3$) 1.40 (14 H, s, C(CH$_3$)$_2$ +NH), 2.67 (4 H, d, J$_1$=1.5 Hz, NCH$_2$), 2.93 (2 H, d, J$_1$=3 Hz, NCH$_2$), 3.72 (1 H, t, J$_1$=.8 Hz, NCH), 7.00 (4 H m, ArH). Anal. (C$_{16}$H$_{28}$N$_2$OS$_2$) C, H, N, S.

EXAMPLE 2

Preparation of Tetraethyl-bis-aminoethanethiol (BAT-TECH)

BAT-TECH was prepared by a method analogous to that disclosed in Example 1, using cyclohexanone in place of o-anisaldehyde as a starting material in Step A. One other difference is that lithium aluminum hydride was employed for the last reduction step of diimine intermediate. The dimercapto hydrochloride salt of BAT-TECH was precipitated and used for this study. Ga-67 was obtained from Mallinckrodt as gallium citrate. Gallium-68 was obtained by eluting a Ge-68/Ga-68 generator with 0.1 N HCl.

EXAMPLE 3

Radiolabeling

No-carrier-added [$^{67}$Ga] citrate (1 mCi/mL) was added to a test tube containing the BAT-TECH ligand (1 mg) in 0.5 mL of water and adjusting the pH to 3.1 by the dropwise addition of a solution of 5% NaOH. The mixture was vortexed and kept in a heating block at 75° C. for 0.5 hour. The percent labeling yield was measured by thin-layer chromatography (Silica gel plate, developing solvent: acetone:acetic acid 3:1, V/V, R$_f$=0.1 and 0.7 for Ga-citrate and Ga-BAT-TECH, respectively). The radiochemical purity usually is over 96%. This material was used directly for animal studies. Effect of acidity and the reaction time on the formation of this complex was determined by the same TLC technique.

For a monkey imaging study,, Ga-68 was eluted from a $^{68}$Ge/$^{68}$Ga generator and extracted in a 6 N HCl solution with ether (3×1.5 mL). The combined extract was dried under a stream of nitrogen To this residue, BAT-TECH ligand (3 mg/mL, pH3.1) was added. The mixture was heated in a heating block at 75° C. for 15 min. After filtration through a 0.22 micron filter, the material was assayed and injected into a monkey. The whole preparation was accomplished in 40 min.

Conductivity data, elemental analysis data, infrared, proton NMR spectroscopy and mass spectral measturements were consistent with the formulation [Fa(BAT-TECH)Cl]. Examination of the IR and NMR data suggest that, as with the Tc=0 analogs of the BAT ligands, complexation occurs by gallium binding to the two sulfur atoms and the two attributable to the SH stretching frequency, which appears as a strong band at 2420 cm$^{-1}$ in the spectrum of the ligand. The proton NMR data (27° C., CDCl$_3$) show resonances for all of the diasterotopic methylene portons adjacent to the nitrogen atoms of the ligand backbone. The observation of well resolved resonances of the individual methylene protons, similar to that observed for proton NMR of the Tc=0 complexes of N$_2$S$_2$ ligands, suggests that the gallium binds to the nitrogen atoms and may impose a rigid structure on an otherwise flexible ligand. Conductivity measurements (0.42 ohm$^{-1}$cm$^2$mol$^{-1}$; 10$^{-3}$M, acetonitrile) indicate that the molecule is neutral in this solvent. The mass spectral data (chemical ionization) show a molecular ion cluster at mz=465 with an isotope distribution pattern in agreement with [M+H]$^+$ (where M=[Ga(BAT-TECH)Cl]) and fragmentation from this molecular ion to give [M-Cl]$^+$, M/Z=430, indicating the cleavage of the chloride ion.

At tracer concentrations, the aqueous chemistry has been studied using [$^{67}$Ga] gallium citrate as the starting material. The net charge in an aqueous solution was found to be +1. The ratio of ligand to $^{67}$Ga was determined to be a:a. Presumably, under the conditions required for the preparation of the $^{67}$Ga complex, the cationic [$^{67}$Ga(BAT-TECH)]$^+$ species is formed. Using reverse phase HPLC (PRP-1 column,; mobile phase=90/10 CH:CN/5mM DMGA, ph-7; flow rate lmL/min), phase=90/10 CH$_3$CN/5mM DMGA, ph-7; flow rate lmL/min), [$^{67}$Ga9BAT-TECH)]$^+$ elutes at 6.5 min., suggesting that the complex is very lipid-soluble.

The partition coefficient of the [$^{67}$Ga(BAT-TECH)]$^+$ complex was measured by mixing the compound with 3 g each of 1-octanol and buffer (pH 7.0 or 7.4, 0.1 M phosphate) in a test tube. This test tube was vortexed for 3 minutes at room temperature and then centrifuged for 5 minutes. Two weighed samples (0.5 g each) from the 1-octanol and buffer layers were counted in a well counter. The partition coefficient was determined by calculating the ratio of counts per minute/gram of octanol to that of buffer. Samples from the octanol layer were repartitioned until consistent partition coefficient values were obtained. The measurement was repeated three times. The partition coefficient of the complex was determined to be 147±5.18 (pH 7.0) and 72.3±3.47 (pH 7.4).

EXAMPLE 4

Biodistribution in Rats

Biodistribution of [$^{67}$Ga]BAT-TECH was studied in male Sprague Dawley rats (200-250 g) which were allowed access to food and water ad lib. Saline solution containing [$^{67}$Ga]BAT-TECH in a volume of 0.2 ml was injected directly into a femoral vein. Rats were sacrificed (at various time points, 2, 30 and 60 min., post injection) by cardiac excision under ether anesthesia. The organs of interest were removed and counted using a well gamma counter. Percent dose per organ was calculated by comparison of tissue counts to suitably diluted aliquots of injected material. Total activities of blood and muscle were calculated assuming that they are 7% and 40% of total body weight, respectively. Each time point consists of a group of three rats.

As shown in Table 1, after an iv injection of [$^{67}$Ga]-BAT-TECH in rats, a significant heart uptake (1.68% dose/organ) at 2 min was observed. The heart uptake dropped to 0.52% dose/g at 30 min and 0.26% dose/g at 1 hour. The heart uptake values are better than those reported for [$^{68}$Ga](5-MeOSal)$_3$TAME (0.97, 0.23 and 0.14% dose/whole heart in rats at 1, 30 and 60 min postinjection, respectively). The heart to lung and heart to blood ratios for this complex are also comparable to or superior to those reported for [$^{68}$Ga](5- MeOSal)-$_3$TAME. There is significant uptake in the liver which does not wash out with time.

TABLE 1

Biodistribution of [$^{67}$Ga]BAT-TECH in rats after an iv injection (% dose/organ)

| Organ | 2 min | 30 in | 60 min |
|---|---|---|---|
| Blood | 10.18 ± 0.30 | 3.58 ± 0.08 | 4.54 ± 1.10 |
| Heart | 1.68 ± 0.12 | 0.52 ± 0.08 | 0.26 ± 0.02 |
| Muscle | 13.89 ± 3.21 | 21.14 ± 2.18 | 10.79 ± 1.85 |
| Lung | 2.07 ± 0.07 | 0.46 ± 0.09 | 0.37 ± 0.009 |
| Kidney | 6.94 ± 0.31 | 2.00 ± 0.10 | 1.06 ± 0.14 |
| Spleen | 0.50 ± 0.06 | 0.15 ± 0.009 | 0.11 ± 0.001 |
| Liver | 21.52 ± 1.11 | 33.54 ± 4.42 | 46.41 ± 2.39 |
| Skin | 5.44 ± 1.65 | 7.56 ± 1.60 | 5.78 ± 0.92 |
| Brain | 0.02 ± 0.004 | 0.01 ± 0.001 | 0.01 ± 0.002 |

2,9-Dimethyl-2,9-mercapto-5-(2-hydroxyphnyl)-4,7-diazadecane was labelled, and the biodistributino of the labelled compound measured, by analogous methods. The results are presented in Table 2.

TABLE 2

Biodistribution of [$^{67}$Ga]2,9-Dimethyl-2,9-Dimercapto-5-(2-hydroxyphenyl)-4,7-diazadecane in rats after an iv injection (% dose/organ)

| Organ | 2 min | 30 min |
|---|---|---|
| Blood | 11.240 ± .724 | 2.823 ± .182 |
| Heart | .940 ± .094 | .380 ± .039 |
| Muscle | 14.392 ± 2.91 | 17.49 ± 1.37 |
| Lung | 1.236 ± .155 | .690 ± .481 |
| Kidney | 5.677 ± .266 | 1.204 ± .080 |
| Spleen | .431 ± .085 | .155 ± .022 |
| Liver | 20.93 ± 4.13 | 25.31 ± 1.09 |
| Skin | .137 ± .023 | .079 ± .004 |
| Brain | .026 ± .002 | .019 ± .001 |
| Brain/Blood | .028 | .073 |

EXAMPLE 5.

Imaging Study in a Monkey

A monkey (10 lb) was sedated with ketamine (50 mg i.m.) and then anesthetized with nembutal (0.2 mL, 25 mg/mL, additional amount was used as needed). The monkey was positioned in the PENN-PET[38]tomograph and the scan started at 7 min after an iv injection of [$^{68}$Ga]BAT-TECH (424 μCi/3 mL of saline). The monkey was scanned for 15 min and a total of 5.8 million counts were collected. Data were reconstructed in 45 overlapping 8 mm thick slices using filtered backprojection with a Hanning filter. In this preliminary study, no attenuation correction was performed. Slice spacing was 2 mm, yielding image data on a 2×2×2 mm grid suitable for displaying transverse, sagittal, or coronal sections.

What is claimed is:

1. Radioisotopic complexes of the formula:

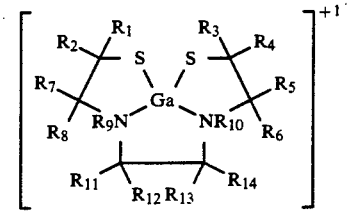

where each of $R_1$-$R_{14}$ is independently selected from the group consisting of hydrogen, C1-C10 alkyl groups in which one or more carbon atoms is optionally substituted by a heteroatom such as N, O or S, and phenyl optionally mono- or di-substituted with a substituent selected from the group consisting of —$SR_{15}$, —$OR_{15}$, and —$NR_{15}R_{16}$, where $R_{15}$ and $R_{16}$ are independently selected from H and C1-C10 alkyl groups; or each grouping of $R_1$ and $R_2$, $R_3$ and $R_4$, $R_5$ and $R_6$, $R_7$ and $R_8$, $R_{11}$ and $R_{12}$, and $R_{13}$ and $R_{14}$ may independently be taken together to form a cyclic C1-C10 alkyl in which one or more carbon atoms is optionally substituted by a heteroatom; Ga is a radioactive gallium isotope; and pharmaceutically acceptable salts thereof.

2. A complex of claim 1 in which the Ga atom is Ga-68.

3. A radioisotopic imaging agent comprising a complex of claim 1.

4. A complex of claim 1 in which, independently, $R_1=R_2$ or may be taken together to form a ring structure; $R_3=R_4$ or may be taken together to form a ring structure; $R_5=R_6$ or may be taken together to form a ring structure; $R_7 = R_8$ or may be taken together to form a ring structure; $R_{11} = R_{12}$ or may be taken together to form a ring structure and $R_{13} = R_{14}$ or may be taken together to form a ring structure.

5. A complex of claim 4 in which the Ga atom is Ga-68.

6. A complex of claim 1 in which $R_5$, $R_6$, $R_8$, $R_{13}$ and $R_{14}$ are each hydrogen.

7. A complex of claim 6 in which the Ga atom is Ga-68.

8. A complex of claim 1 in which each of $R_1$, $R_2$, $R_3$ and $R_4$ is ethyl group.

9. A complex of claim 8 in which the Ga atom is Ga-68.

10. A complex of claim 1 in which $R_{11}$ and $R_{12}$ are taken together to form a ring structure.

11. A complex of claim 10 in which the Ga atom is Ga-68.

12. A complex of claim 1 in which $R_{11}$ and $R_{12}$ are taken together to form a cyclohexyl group.

13. A complex of claim 12 in which the Ga atom is Ga-68.

14. A complex of claim 1 in which $R_5$, $R_7$, $R_8$, $R_{13}$ and $R_{14}$ are each hydrogen and in which each of $R_1$, $R_2$, $R_3$ and $R_4$ is an ethyl group.

15. A complex of claim 14 in which the Ga atom is Ga-68.

16. A complex of claim 14 in which $R_{11}$ and $R_{12}$ are taken together to form a cyclohexyl group.

17. A complex of claim 16 in which the Ga atom is Ga-68.

* * * * *

UNITED STATES PATENT AND TRADEMARK OFFICE
CERTIFICATE OF CORRECTION

PATENT NO. : 5,079,346            Page 1 of 3
DATED : January 7, 1992
INVENTOR(S) : Kank F. Kung It is certified that error appears in the above-identified patent and that said Letters Patent is hereby corrected as shown below:

On the title page,

Item [56], Line 29 delete "(triosemicarbazone)" and insert therefor --(thiosemicarbazone)--.

Column 2, Line 47 delete "$N_2S_2$ligand" and insert therefor --$N_2S_2$ ligand--.

Column 4, Line 25 delete "R$^1$" and insert therefor --$R_1$--

Column 4, Line 33 delete "[Ga(BAT-TECH)]$^=$complex" and insert therefor --[Ga(BAT-TECH)]$^+$ complex--.

Column 4, Line 34 delete "(GA$^{=3}$)" and insert therefor --(GA$^{+3}$)--.

Column 4, Line 42, delete "both" and insert therefor --Both--.

Column 5, Line 17, delete "99m" and insert therefor --Tc-99m--.

Column 5, Line 21 delete "methoxybenzen-acetonitrile" and insert therefor --methoxybenzenacetonitrile--.

Column 5, line 34, delete "o-amino" and insert therefor --α-amino--.

Column 5, line 38 delete "(CDCL$_3$)" and insert therefor --(CDCl$_3$)--.

UNITED STATES PATENT AND TRADEMARK OFFICE
CERTIFICATE OF CORRECTION

PATENT NO. : 5,079,346
DATED : January 7, 1992
INVENTOR(S) : Kank F. Kung

It is certified that error appears in the above-identified patent and that said Letters Patent is hereby corrected as shown below:

Column 6, line 11 delete "methoxybenzene-ethanamine" and insert therefor --methyoxybenzeneethanamine--.

Column 6, Line 17 delete "α-anisaldehyde" and insert therefor --o-anisaldehyde--.

Column 6, Line 66 delete "4,58" and insert therefor --4.58--

Column 7, Line 1 delete "preparation" and insert therefor --Preparation--.

Column 7, Line 23 delete "NCH,)" and insert therefor --NCH$_2$)--.

Column 7, Line 28 delete "merapto" and insert therefor --mercapto--.

Column 8, Line 2 delete "generator" and insert therefor --generator$^+$--.

Column 8, Line 21 delete "study,," and insert therefor --study,--.

Column 8, Line 31 delete "measture-ments" and insert therefor --measurements--.

Column 8, Line 36 after the words "and the two" insert --nitrogen atoms. The IR data of the complex show no band--.

Column 8, Line 64 delete "CH:CN/5mM" and insert therefor --CH$_3$/CN/5mM--.

Column 8, Line 65 delete "phase=90/10 CH$_3$CN/5mM DMGA, ph-7; flow rate 1mL/min),"

UNITED STATES PATENT AND TRADEMARK OFFICE
CERTIFICATE OF CORRECTION

PATENT NO. : 5,079,346
DATED : January 7, 1992
INVENTOR(S) : Kank F. Kung

It is certified that error appears in the above-identified patent and that said Letters Patent is hereby corrected as shown below:

Column 9, Line 10 delete "minute/-" and insert therefor --minute/--.

Column 9, Line 65 delete "(2-hydroxyphnyl)" and insert therefor --(2-hydroxyphenyl)--.

Column 10, lines 36-36
Claim 1, delete                and insert therefor

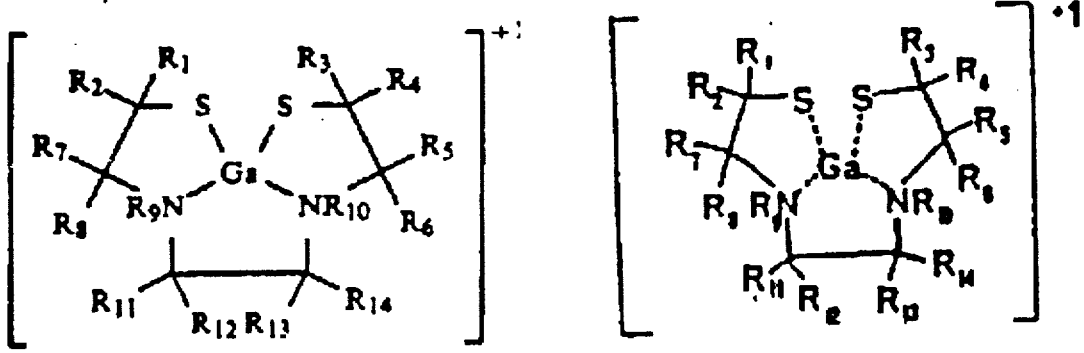

Signed and Sealed this

Twenty-sixth Day of October, 1993

Attest:

BRUCE LEHMAN

Attesting Officer    Commissioner of Patents and Trademarks